United States Patent [19]
Hizuka

[11] Patent Number: 5,786,896
[45] Date of Patent: Jul. 28, 1998

[54] OBLIQUE INCIDENCE INTERFEROMETER WITH FRINGE SCAN DRIVE

[75] Inventor: Masatoshi Hizuka, Omiya, Japan

[73] Assignee: Fuji Photo Optical Co., Ltd., Omiya, Japan

[21] Appl. No.: 650,994

[22] Filed: May 21, 1996

[30] Foreign Application Priority Data

May 23, 1995 [JP] Japan ................................ 7-146931

[51] Int. Cl.$^6$ ........................................................ G01B 9/02
[52] U.S. Cl. .............................................. 356/354; 356/359
[58] Field of Search ................................. 356/354, 359

[56] References Cited

U.S. PATENT DOCUMENTS

| | | | |
|---|---|---|---|
| 4,707,137 | 11/1987 | Lee | 356/354 |
| 5,568,256 | 10/1996 | Korner et al. | 356/354 |

OTHER PUBLICATIONS

"Improved Oblique–Incidence Interferometer", Hawhanan, Optical Engineering, S–1975, pp. 257–258.

*Primary Examiner*—Samuel A. Turner
*Attorney, Agent, or Firm*—Oblon, Spivak, McClelland, Maier & Neustadt, P.C.

[57] ABSTRACT

An oblique incidence interferometer capable of fringe scanning by use of a fringe scan drive association with a first or second diffraction grating member of the interferometer to drive the associated grating member step by step over a micrometric distance in a direction perpendicular to a path of light in travel in a straightforward direction. Laser light from a light source 20 is diffracted into a zero order diffraction wave L1 in travel in a straightforward direction and a +1 order diffraction wave L2 by a first diffraction grating member 26 of a grating assembly 41. The grating assembly 41 is vertically movably supported on a surface plate 42 by a pair of level support members 43 each having a stratified leaf spring structure. The grating assembly 41 sits on a piezoelectric actuator 45 which serves as a fringe scan drive for driving the first diffraction grating member 26 over a micrometric distance in the vertical direction. As the first diffraction grating member 26 is moved in a direction perpendicular to the light path of incident light, +1 order diffraction wave incident on a specimen 28 is shifted in phase, causing a displacement of a predetermined extent to interference fringes as observed through an image sensor 32.

2 Claims, 3 Drawing Sheets

5,786,896

OBLIQUE INCIDENCE INTERFEROMETER WITH FRINGE SCAN DRIVE

BACKGROUND OF THE INVENTION

1. Field of the Art

This invention relates to an oblique incidence type interferometer using obliquely incident light in testing surface conditions of a specimen by way of interference fringes, and more particularly to an oblique incidence type interferometer which is provided with a micrometric drive means in association with a diffraction grating for the purpose of fringe scanning.

2. Prior Art

Heretofore, interferometers have been widely resorted to as non-contacting test means in inspecting surface conditions of precision products such as optical elements or the like. Shown in FIG. 3 is a Fizeau interferometer typical of the interferometers of the sort as mentioned above.

In this figure, the interferometer which is generally indicated at 1 includes a laser light source 2 and, in the light path of a laser beam from the laser light source 2, a reflector mirror 3, a diverging lens 4 and a pinhole 5. The laser beam from the light source 2 is turned through 90° by the reflector mirror 3 and passed through the diverging lens 4 and the pinhole 5, which is located at the converging point of the diverging lens 4 so that the beam spot past the pinhole 5 is spread toward a beam splitter 6. At the beam splitter 6, the laser beam is turned through 90° again to travel on in a direction opposite to the direction of beam projection from the laser light source 2. The laser beam is then collimated through a collimator lens 7 and shed on a reference plate 8 which is located in position forward of the collimator lens 7.

The reference plate 8 is provided with a precision finish plane reference surface 8b on the side away from its light incident surface 8a which is covered with an anti-reflection coating. The laser beam incident on the reference plate 8 is partly reflected off the reference surface 8b while the remainder is transmitted through the reference plate 8 toward a testing surface 9a of a specimen 9 which is set in position forward of the reference plate 8. The laser beam incident on the specimen 9 is partly reflected off the testing surface 9a and superposed on a reflected light wave from the reference surface 8b to produce interference fringes by the interference between the two reflected light waves from the testing surface 9a and the reference surface 8b. The light reflections containing such interference fringes are projected on a screen 10 through the collimator lens 7 and beam splitter 6, and an image of interference fringes on the screen 10 is taken by an image sensor 12 through an interference fringe imager lens 11 to check surface conditions of the specimen 9 under inspection by way of an image of interference fringes displayed on a monitor screen.

With an interferometer which is arranged as described above, no interference fringe is observed when the testing surface 9a of the specimen 9 is finished to perfect accuracy, namely, when the testing surface 9a is finished perfectly in an shape absolutely identical with the reference surface 8b, while a larger number of interference fringes are observed when the testing surface 9a contains a greater degree of deviations from the reference surface in shape or contour. In other words, the accuracy of the testing surface 9a of the specimen 9 can be measured by the number of interference fringes.

Through observation of interference fringes, one can grip the surface condition of the specimen 9 with regard to the shape or contour of the testing surface 9a as a whole, excepting data of surface irregularities or undulations in certain localities. The surface accuracy in certain localities of the testing surface 9a can be measured by the use of the so-called fringe scanning based on phase shifts. Fringe scanning is a method of analyzing interference fringes, in which interference fringes are shifted by moving a reference surface little by little in a submicrometric level while measuring variations in light intensity at a number of points to analyze phasic relations between the respective measuring points.

In order to carry out fringe scanning on the interferometer of FIG. 3, either the reference plate 8 or the specimen 9 is moved little by little in the direction of the optical axis. In so doing, in case the laser light source 2 is of a wavelength of $\lambda$, the reference plate 8 or the specimen 9 needs to be moved over a distance of $\lambda/2$ on a driving stroke because one interference fringe occurs at every $\lambda/2$ measure of surface variations along the contour of the testing surface 9a of the specimen 9. More specifically, in a case where the light source 2 is a He-Ne laser having a wavelength of 632.8 nm, the reference plate 8 or the specimen 9 needs to be moved over a distance of $\lambda/2=316.4$ nm each time, for example, by four steps making a distance of 79 nm in each step, in other words, progressively in a pitch of 79 nm. A picture image of interference fringes is taken through the image sensor 12 at each shifted position to detect the light intensity in each pixel of the image sensor 12, displaying on a monitor screen a three-dimensional surface configuration of the specimen by way of a contour map or other graphic image.

With a Fizeau type interferometer, which permits to observe one interference fringe at each $\lambda/2$ measure along a rising or falling contour on the testing surface 9a of the specimen 9 as mentioned above, however, difficulties have been experienced in that interference fringes often come out in an abnormally high density due to an inherently high sensitivity to surface variations, rendering the testing operation substantially infeasible particularly in those cases the testing surface 9a of the specimen 9 contains surface variations of a relatively large scale along its contour. In addition, the normal angle of light incidence makes the measurement infeasible in some cases, for example, in a case where the specimen 9 is of a material which has such a high transparency or of such a low reflectivity as to be able to reflect off only an extremely small amount of light at its testing surface 9a.

In view of the problems as mentioned above, it has been the general practice in the art to employ the so-called oblique incidence type interferometers particularly for specimens which contain variations of a relatively large scale along a surface contour to be tested or for specimens of low reflectivity. Shown in FIG. 4 is typical optical arrangements in such oblique incidence type interferometers.

As shown in FIG. 4, a laser beam from a laser light source 20 is turned by a reflecting prism 21 and passed through a diverging lens 22 and a pinhole 23 toward a reflector mirror 24. The diverging light flux from the reflector mirror 24 is collimated through a collimator lens 25 to project a collimated light flux toward a first diffraction grating member 26 for diffraction of light.

In this instance, on the output side of the first diffraction grating member 26, directly transmitted light, namely, a zero order diffraction light wave $L_1$ and +1 order diffraction light wave $L_2$ are used for the measurement. Zero order diffraction light $L_1$ is used as a reference wave, while +1 order diffraction light $L_2$ is shed on a specimen 28 which is set in position on a specimen holder table 27. The +1 diffraction wave $L_2$ is shed on the specimen 28 obliquely at a predetermined angle of incidence to reflect off an object light wave $L_3$. A second diffraction grating member 29 is located at a position where light paths of the object wave $L_3$ and reference wave $L_1$ intersect with each other. The object light $L_3$ and reference light $L_1$ are diffracted again at the second diffraction grating member 29 in such a way that a directly transmitted zero order wave $L_4$ of the object light is superposed on a $-1$ order diffraction wave $L_5$ of the reference light $L_1$. Accordingly, interference takes place between the wave fronts of zero order diffraction light $L_4$ of the object light and $-1$ order diffraction light $L_5$ of the reference light to produce interference fringes. An interference fringe observation means similar to the one as in the above-described Fizeau interferometer is provided in the path of the superposed light waves which contain the interference fringes. More specifically, a picture image of interference fringes is projected on a screen 30, and the image on the screen 30 is picked up by an image sensor means 32 through an interference fringe imager lens 31. In this case, the imaging plane of the screen 30 is positioned parallel with the testing surface of the specimen 28 and in face to face relation with the fringe imager lens 31 and the image sensor means 32. Denoted at 33 is a photosensitive element which is provided for alignment purposes.

The first and second diffraction grating members 26 and 29 are constituted, for example, by holographic optical elements which are fabricated by coating a photoresist film on a glass substrate, and exposing the photoresist film by electron beam scanning to a holographic pattern equivalent to interference fringes as produced by object and reference light waves, followed by development of the holographic pattern of interference fringes. The holographic optical element of this sort is capable of reproducing an object light wave upon projecting a reproduced reference wave on the interference fringes of the holographic pattern.

The oblique incidence type interferometer, which is arranged to project light obliquely on a specimen 28 as described above, makes it possible to test even specimens of high transparency because of an increased amount of light reflection off the testing surface of the specimen 28, that is to say, because it can give off an increased amount of object light as compared with the normal incidence type.

Besides, as shown in FIG. 5, in the case of an oblique incidence interferometer, generally a relationship of $\sin \theta / \lambda = 1/d$ can be established, where d is the pitch of the holographic grating G on the first diffraction grating member 26, $\theta$ is the diffraction angle of +1 order diffraction light and $\lambda$ is the wavelength of the laser light source 20. In case a specimen contains a falling or rising surface variation of a measure h in its contour, a shift $\Delta l$ occurs to the light path of +1 order diffraction light according to the scale of the falling or rising surface variation, namely, as expressed by an equation $\Delta l = 2h \cdot \sin \theta$. If one interference fringe is to be produced by this shift of the light path, we should have $\Delta l = 2h \cdot \sin \theta = \lambda$ and therefore $h = \lambda/2 \sin \theta = d/2$. Accordingly, in the case of an interferometer where the laser light source 20 has a wavelength of 632.8 nm and the first diffraction grating member 26 has a grating pattern G with a pitch width of 4 nm, it will have a diffraction angle $\theta$ of 9.1 degrees for +1 order diffraction light and sensitivity of 2 μm. Namely, it can be conveniently used particularly for testing surfaces which contain variations of a relatively large scale in contour or shape.

For inspecting surface conditions by way of interference fringes, the so-called fringe scanning is feasible in the case of a normal incidence type Fizeau interferometer, by moving in the direction of an optical axis either one of reference and testing surfaces, which are disposed face to face with each other and at right angles with the optical axis. However, it has been considered infeasible to conduct fringe scanning in the case of an oblique incidence type interferometer in which a testing surface is positioned obliquely relative to an optical axis of incident light and therefore needs to be moved in an oblique direction for a shift in the direction of the optical axis, necessitating to move a plural number of other component parts to cope with a shift of the optical axis of reflected light off the testing surface, which would also result from the shift of the testing surface. For these reasons, heretofore it has been difficult to apply the fringe scanning to oblique incidence type interferometers.

SUMMARY OF THE INVENTION

In view of the foregoing situations, it is an object of the present invention to make fringe scanning feasible on an oblique incidence type interferometer in testing surface conditions of a specimen by way of interference fringes.

In accordance with the present invention, the above-stated objective is achieved by the provision of an oblique incidence interferometer incorporating a fringe scan drive means in association with either a first diffraction grating member or a second diffraction grating member for shifting same over a micrometric distance in a direction perpendicular to a straightforward travel direction of incident light from a light source.

More particularly, according to the invention, there is provided an oblique incidence type interferometer, including a light source, a first diffraction grating member located in a light path from the light source to diffract incident light rays into a reference wave in travel in a straightforward direction therethrough and a diffracted wave having a predetermined angle with respect to the reference wave, a specimen holder table so located as to hold a specimen in position for reflecting off the diffraction wave from the first diffraction grating member, a second diffraction grating member located at an intersection of the reference wave and an object wave reflected off a testing surface of the specimen on the specimen holder table to superpose wave fronts of the reference and object waves, and an interference fringe observation means including means for imaging interference fringes produced by interference between the wave fronts of the reference and object waves, characterized in that the oblique incidence type interferometer includes a fringe scan drive means provided in association with either one of the first and second diffraction grating members for shifting same step by step over a predetermined micrometric distance in a direction perpendicular to a straightforward travel direction of incident light from the light source.

For example, in a case where the drive means is coupled with the first diffraction grating member, +1 order diffraction wave of incident light, which falls on a testing surface of a specimen, is shifted in phase upon moving the first diffraction grating member. As a consequence, it becomes possible to obtain data of surface conditions of the specimen, especially of minute surface variations or undulations by firstly taking a picture image of interference fringes before actuating the fringe scan drive means and then shifting the first diffraction grating member little by little over a micrometric distance by a plural number of steps while taking a picture image of the interference fringe in each shifted position.

The above and other objects, features and advantages of the invention will become apparent from the following particular description of the invention, taken in conjunction with the accompanying drawings which show by way of example a preferred embodiment of the invention.

DESCRIPTION OF PREFERRED EMBODIMENTS

Figure 1:
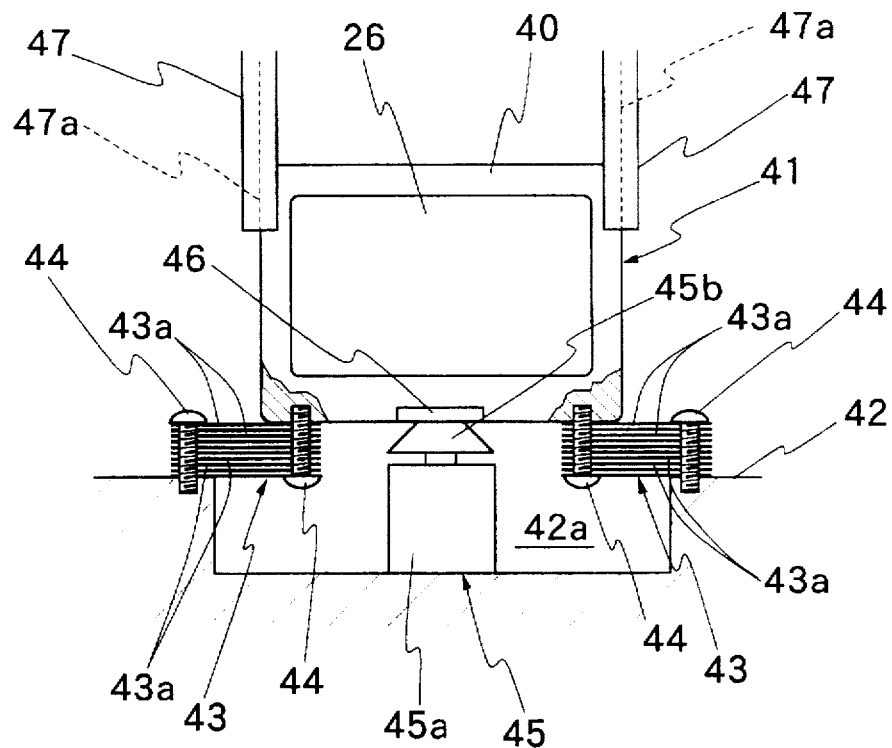
FIG. 1 is a schematic view of a fringe scan drive mechanism embodying the present invention.
Figure 2:
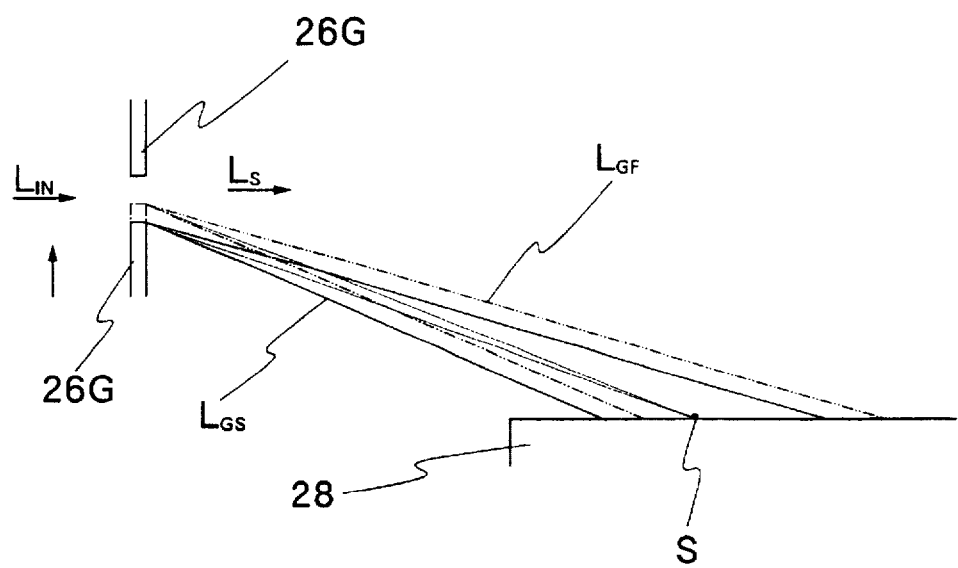
FIG. 2 is a diagrammatic illustration explanatory of principles of causing a phase shift to a diffracted wave obliquely incident on a testing surface of a specimen under inspection on an oblique type incidence interferometer.
Figure 3:
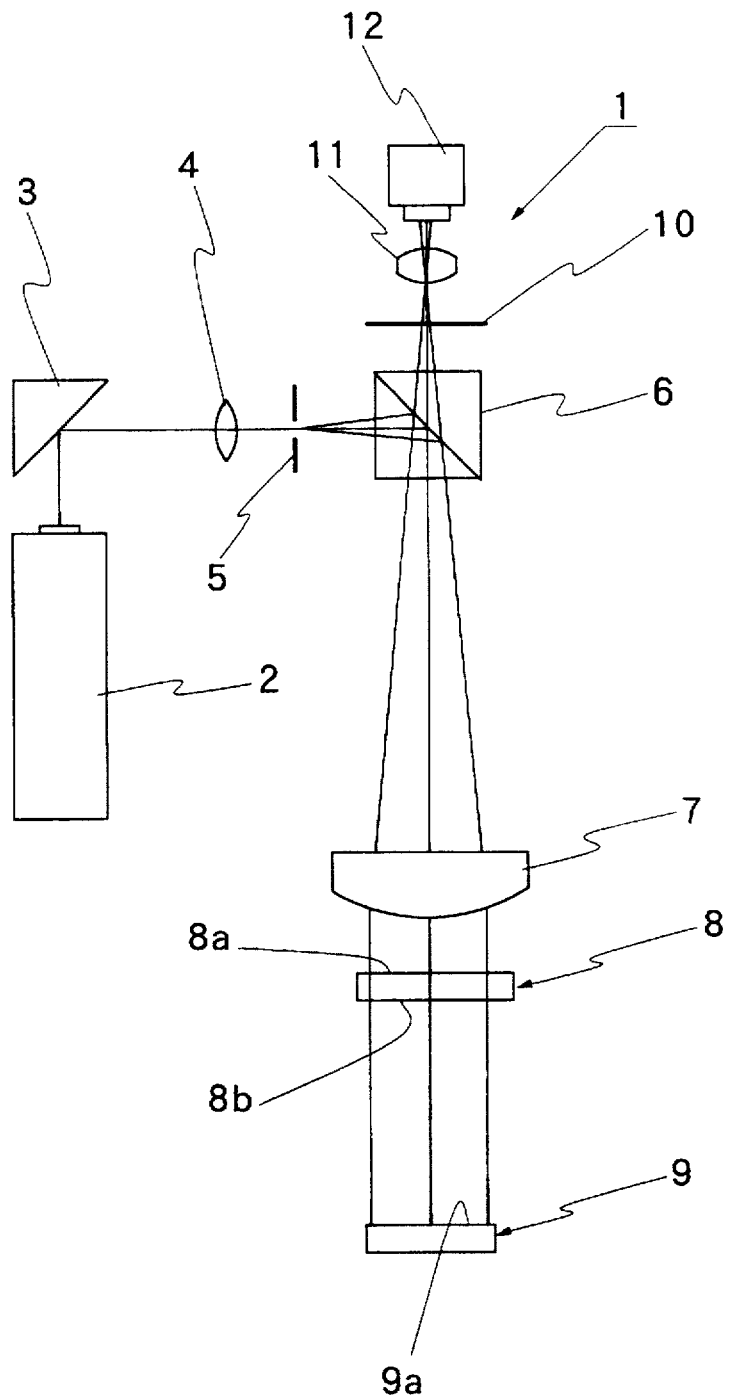
FIG. 3 is a diagrammatic view of a Fizeau type interferometer shown as a typical example of normal incidence type interferometers generally in use for measuring surface conditions of specimens.
Figure 4:
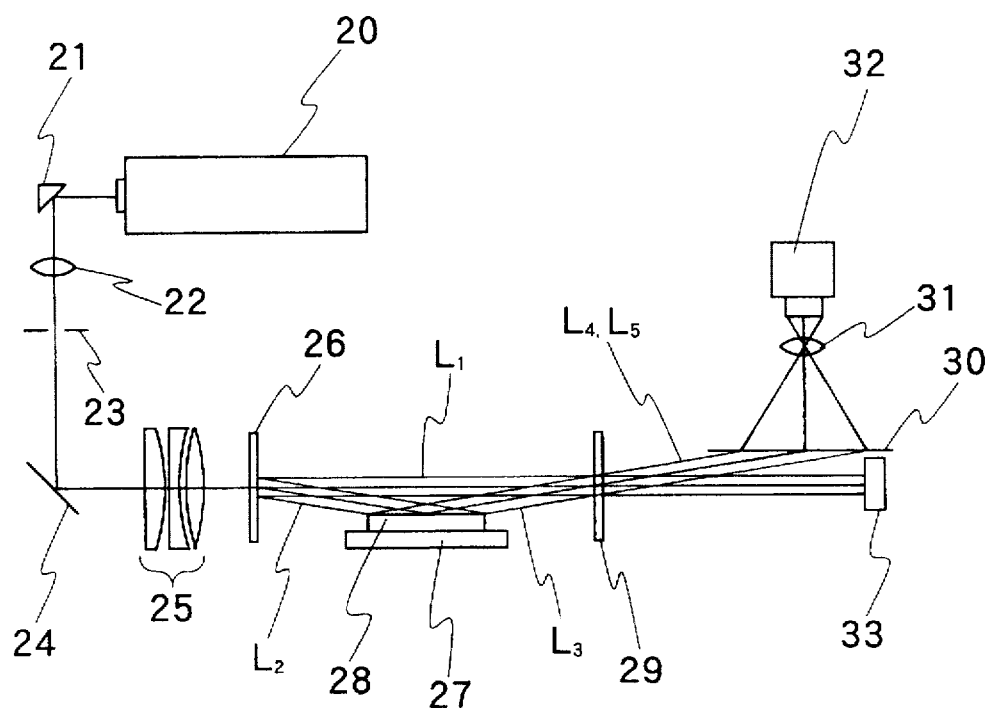
FIG. 4 is a diagrammatic view of an oblique incidence interferometer, showing its general arrangements.
Figure 5:
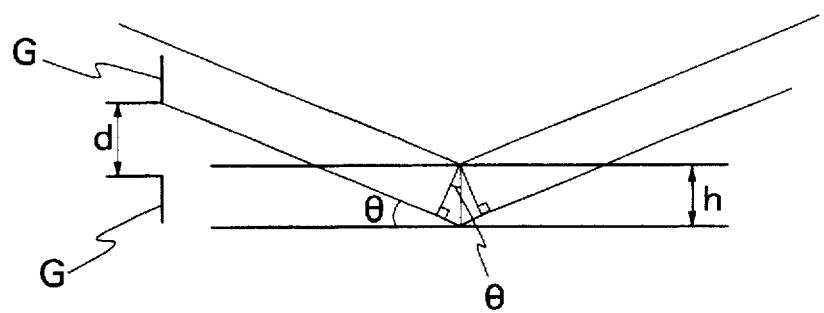
FIG. 5 is a diagrammatic illustration explanatory of arithmetic expressions used in determining the sensitivity of the oblique incidence interferometer.

Now, the invention is described more particularly by way of its preferred embodiments with reference to FIGS. 1 and 2 of the accompanying drawings. In the following description, the construction of an oblique incidence interferometer itself is not explained in detail because it is fundamentally same as in FIG. 4. In the embodiment of FIGS. 1 and 2, by way of example a fringe scan drive means is shown as being coupled with a first diffraction grating member 26.

More specifically, shown in FIG. 1 is a drive mechanism for the first diffraction grating member 26, which causes a shift in phase as will be explained below with reference to FIG. 2.

In FIG. 2, indicated at 26G is a holographic grating pattern of the first diffraction grating member 26. When the holographic grating pattern 26G is in the position indicated by solid line in FIG. 2, incident light $L_{IN}$ is separated into straight directly transmitted light $L_s$ and +1 order diffraction light $L_{GS}$. In this state, even if the holographic grating pattern 26G is shifted in the arrowed direction into a position indicated by imaginary line, the light path of the directly transmitted light $L_s$ remains unchanged, that is to say, remains in the same travel direction as $L_s$ since the holographic grating pattern 26G is being moved in a direction perpendicular to the optical axis. However, the light path of +1 order diffraction light is shifted as indicated at $L_{GF}$, which is different in length from the original light path $L_{GS}$ between the first diffraction grating member 26 and a testing surface position S where the specimen 28 is located. Therefore, the phase of incident light on the testing surface S is shifted depending upon the degree of difference in the light path length. Accordingly, a fringe scanning operation becomes feasible by shifting the position of the first diffraction grating member 26 over a micrometrical distance in the vertical direction, namely, in a direction perpendicular to the straightforward travel direction of light incident on the diffraction grating member 26 from the laser light source 20.

As shown particularly in FIG. 1, the first diffraction grating member 26 is fitted in a frame body 40 to form a diffraction grating assembly 41, which is in turn mounted on a surface plate 42 together with and independently of other optical parts. In the particular embodiment shown, the diffraction grating assembly 41 is indirectly supported on the surface plate 42 and bridged over a mounting recess 42a of the surface plate 42 through a couple of level support members 43 which are extended inward from stepped wall portions on the opposite sides of the mounting recess 42a of the surface plate 42. The level support members 43 are required to be able to support the total weight of the diffraction grating assembly 41 in a horizontal state free of deformations, and at the same time required to be movable vertically in the upward direction upon application of an external drive force. For these reasons, in the embodiment shown, the support members 41 are each constituted by a suitable number of leaf springs 43a which are superposed one on another to form a stratified structure and fixed to the frame member 40 and the surface plate 42 by bolts 44 or other suitable fixation means.

For the purpose of moving the diffraction grating assembly 44 minutely in the upward and downward directions, a piezoelectric actuator 45 which incorporates a piezoelectric element is provided to serve as the afore-mentioned fringe scan drive means. This piezoelectric actuator 45 has a piezoelectric element (not shown) housed in a casing 45a in association with a pusher 45b which is contractably extensible in the vertical direction. The pusher 45b is abutted at its upper end against a rigid bottom cover plate 46 which is fixed securely and centrally on the bottom side of the frame body 40 of the diffraction grating assembly 41. By applying a voltage to the piezoelectric element within the casing 45a, the pusher 45b is stretched step by step over a micrometrically fine stroke range which is smaller than 1 micrometer. In FIG. 1, the reference numeral 47 indicates a pair of guide posts serving as a guide for the vertical movements of the diffraction grating assembly 41, the guide posts 47 being provided with channel-like guide grooves 47a which embrace the opposite lateral sides of the frame body 40 to prevent same from displacing in a falling direction as the diffraction grating assembly 41 is moved by the piezoelectric actuator 45.

In order to test the surface conditions of a specimen 28 which is set in position on a specimen holder table 27, a laser beam is projected from the laser light source 20 toward the first diffraction grating member 26, which is supported on the fringe scan drive means of the arrangements as described above. More specifically, firstly while holding the first diffraction grating member 26 in a predetermined original position with the piezoelectric actuator 45 in de-energized state, a picture image of interference fringes on the screen 30 is taken and observed through the image sensor means 32 to inspect the surface conditions of the specimen 28.

Then, in order to start fringe scanning after taking the picture image of interference fringes at the original position, a predetermined voltage is applied to the piezoelectric actuator 45, causing the pusher 45b to stretch by a predetermined micrometric length through deformation of the piezoelectric element. As a result, the first diffraction grating member 26 is slightly moved in a direction perpendicular to a straightforward travel direction of incident light from the light source, shifting the phase of +1 order diffraction wave $L_2$ incident on the testing surface of the specimen 28. At this time, by the shift of phase, an image of interference fringes taken through the image sensor means 32 is displaced in a predetermined degree. Thereafter, the first diffraction grating member 26 is pushed up step by step for a plural number of times by the piezoelectric actuator 45, while taking picture images of interference fringes successively in the respective shifted positions through the image sensor means 32. In this instance, in order to set the sensitivity of the interferometer at 2 micrometer, for example, suitably the first diffraction grating member 26 is pushed up over the distance of 2 micrometer step by step, more specifically, by four steps or in a pitch of 0.5 μm.

A plural number of picture images of interference fringes thus obtained are analyzed according to a predetermined algorism to display on a monitor screen the test results including information regarding defects in uniformity of shape which are attributable to local surface irregularities or undulations along the contour of the specimen 28.

Of course, instead of moving the first diffraction grating member 26 as in the above-described embodiment, a similar diffraction grating drive means may be provided for the second diffraction grating member 29 to shift same in a direction perpendicular to the optical axis of the reference wave. In such a case, a shift in phase occurs to the reference wave in relation with a micrometric movement of the second diffraction grating member 29. Further, the fringe scan actuator which is required to operate in a micrometric level in terms of stroke length may be constituted by a drive means other than the piezoelectric element as described above, for example, may be constituted by a combination of a stepping motor and a cam or the like.

As clear from the foregoing description, the present invention makes it possible to conduct fringe scanning on an oblique incidence type interferometer by providing a fringe scan drive means in association with a first or second diffraction grating member of the interferometer in such a way as to shift the position of the first or second diffraction grating member stepwise in a micrometrically fine pitch in a direction perpendicular to a straightforward travel direction of incident light from a light source.

What is claimed is:

1. An oblique incidence type interferometer, including a light source, a first diffraction grating member located in a light path from said light source to diffract incident light rays into a reference wave in travel in a straightforward direction therethrough and a diffracted wave having a predetermined angle with respect to said reference wave, a specimen holder table so located as to hold a specimen in position for reflecting off said diffraction wave from said first diffraction grating member, a second diffraction grating member located at an intersection of said reference wave and an object wave reflected off a testing surface of said specimen on said specimen holder table to superpose wave fronts of said reference and object waves, and an interference fringe observation means including means for imaging interference fringed produced by interference between the wave fronts of said reference and object waves, said oblique incidence type interferometer comprising:

a fringe scan drive means provided in association with either one of said first and second diffraction grating members for driving said either one of said first and second diffraction grating to shift a path of diffraction light of +1 order stepwise precisely by a distance smaller than a wavelength of laser light from said light source in a direction perpendicular to a straightforward travel direction of incident light from said light source.

2. An oblique incidence type interferometer as defined in claim 1, wherein said fringe scan drive means is constituted by a piezoelectric actuator employing a piezoelectric element as a micrometric drive member, and said first or second diffraction grating member is fitted in a frame body and vertically movably supported on a surface plate through level support members each having a stratified leaf spring structure.

* * * * *